(12) United States Patent
Cohen et al.

(10) Patent No.: US 11,141,610 B2
(45) Date of Patent: Oct. 12, 2021

(54) HAIR MODIFICATION SYSTEM

(71) Applicant: 2B1K IMPORTS PTY LTD, Sydney (AU)

(72) Inventors: Ben Jan Cohen, Sydney (AU); Benny Risher, Sydney (AU); Kobi Bokshish, Sydney (AU)

(*) Notice: Subject to any disclaimer, the term of this patent is extended or adjusted under 35 U.S.C. 154(b) by 0 days.

(21) Appl. No.: 16/970,505

(22) PCT Filed: Jul. 23, 2019

(86) PCT No.: PCT/AU2019/050771
§ 371 (c)(1),
(2) Date: Aug. 17, 2020

(87) PCT Pub. No.: WO2020/097665
PCT Pub. Date: May 22, 2020

(65) Prior Publication Data
US 2020/0376304 A1 Dec. 3, 2020

(30) Foreign Application Priority Data

Nov. 15, 2018 (AU) ................. 2018904356
May 7, 2019 (AU) ................. 2019901545

(51) Int. Cl.
*A61Q 5/10* (2006.01)
*A61Q 5/06* (2006.01)
*A45D 7/00* (2006.01)
*A61K 8/92* (2006.01)

(52) U.S. Cl.
CPC ............... *A61Q 5/10* (2013.01); *A61Q 5/065* (2013.01); *A45D 2007/001* (2013.01); *A61K 8/922* (2013.01); *A61K 2800/432* (2013.01)

(58) Field of Classification Search
CPC .......... A61Q 5/10; A61Q 5/065; A61K 8/922; A61K 2800/432; A45D 19/022; A45D 2007/001
USPC ............................................. 8/405
See application file for complete search history.

(56) References Cited

FOREIGN PATENT DOCUMENTS

| EP | 2977041 | 1/2016 | |
|---|---|---|---|
| EP | 2957324 | 9/2017 | |
| WO | 2017/088175 | 6/2017 | |
| WO | 2017/124154 | 7/2017 | |
| WO | WO 2017/124154 A1 * | 7/2017 | ............... A61Q 5/10 |

OTHER PUBLICATIONS

International Search Report for PCT/AU2019/050771 dated Oct. 9, 2019, 3 pgs.

* cited by examiner

*Primary Examiner* — Eisa B Elhilo
(74) *Attorney, Agent, or Firm* — Lowenstein Sandler LLP

(57) ABSTRACT

The present invention relates to hair modification system including a range of hair colour modifiers and associated hair modification process and regime. The invention has been developed primarily for use by hair care professionals in a salon environment, but is not limited to this particular field of use.

10 Claims, No Drawings

HAIR MODIFICATION SYSTEM

FIELD OF THE INVENTION

The present invention relates to hair modification system including a range of hair colour modifiers and associated hair modification process and regime.

The invention has been developed primarily for use by hair care professionals in a salon environment, but is not limited to this particular field of use.

BACKGROUND OF THE INVENTION

Any discussion of the prior art throughout the specification should in no way be considered as an admission that such prior art is widely known or forms part of common general knowledge in the field.

The majority of hair modification processes (such as treatments and colours) to date have been based on a discontinuous process of first adding a viscous liquid or semi-solid cream preparation, followed by an incubation time and a thorough cleansing and/or rinsing to remove the preparation. These processes are time-consuming, use a lot of water, and often, there is colour or treatment residue left behind on the scalp and hair even after a thorough cleanse.

While there are systems available that offer means of applying some forms of colouring product during the hair wetting process, these have limitations, such as inefficient dying of the hair, little permanency and uneven colouring.

Similarly, while there are systems available that offer means of applying some form of water conveyed conditioner or cleanser product during the hair wetting process, these have limitations. For example, products that automatically deliver liquid cleansers into fixed bathroom shower heads do not provide any dosage control and cannot be directed in a controlled manner to different regions of the hair and scalp.

It is an object of the present invention to overcome or ameliorate the above discussed disadvantages of the prior art, or at least offer a useful alternative.

SUMMARY OF THE INVENTION

According to a first aspect the present invention provides a method of modifying the colour of hair using a dose of water dispersed hair colour modifier from a water dispersible composition.

In a second aspect of the invention, there is provided a water dispersible composition comprising a hair colour modifier, a thickening agent, and emulsifier and a rheology modifier.

By appearance is meant that the modifier may modify the colour or condition of the hair, wherein the condition may refer to the cleanliness, health, texture and/or shine of the hair.

Accordingly, in embodiments of the invention, the method is a method of modifying the colour of hair using a dose of water dispersed colour modifier from a water dispersible composition. In other embodiments of the invention, the method is a method of modifying the condition of hair using a dose of water dispersed condition modifier from a water dispersible composition.

By "water dispersible" is meant the composition will separate relatively uniformly in a water, to produce a dose of water dispersed hair modifier without significant observable aggregation and/or agglomeration. The water dispersible composition may be solid or a semi-solid substance such as a powder, a milled substance, granulated substance, slurry or paste.

The water dispersible composition may be compressed into the form of a water-disintegrable tablet. By "water-disintegrable" is meant that the tablet will disintegrate when exposed to a flowing, agitated or moving source of said dose of water over a period of time. It would be understood that components of the water dispersible composition and/or water disintegratable tablet may be dissolvable (i.e., soluble) in water, though it is not essential that all components be water soluble for the composition to disperse or the tablet to disintegrate and subsequently disperse.

In embodiments of the invention, the composition is contained in a porous bag or packet made of a thin, light weight porous material that allows water to flow through it. Non-limiting examples include filter paper, or fabric with an open weave, gauze, cheesecloth, mesh, monk's cloth or muslin or the like, and may resemble a teabag. The material may be synthetic or natural.

The water dispersible composition may be dispersed in a dose of water to produce a dose of water dispersed hair modifier at any suitable time prior to, or during, the dose of water dispersed colourant or conditioner being applied to the hair to modify the colour or condition of said hair.

Preferably, the dose of water is supplied as a flowing source of water, and the water dispersible composition and flowing water may be configured such that during use with a flowing water supply at pressure that may be achieved from a domestic tap, the composition may take around 10 seconds to 10 minutes to disperse, dissolve and/or disintegrate and provide a flow of water dispersed hair modifier to a user. Examples of typical water pressure include a pressure range of 10-350 KPa, temperature range of 10-50 degrees Celsius and outlet flow rate of 1-16 litres per minute, preferably 2-8 litres per minute as may be controlled by a flow regulator. In this embodiment of the invention, the water dispersible composition is effectively being dispersed in the dose of water immediately prior to, or almost simultaneously as, the water dispersed colour or condition modifier is being applied to the hair.

The water dispersible composition and source of water may be configured in any way that allows for the composition be substantially captured but allows for the water to substantially flow through as the composition is dispersed in the dose of water. For example, the water dispersible composition may be, completely, substantially or partially contained in a pervious vesicle that allows water to flow through it, thereby dispersing the water dispersible composition into the water to produce the dose water dispersed hair modifier. In the event the composition was in the form of a water disintegrable tablet or contained in a porous bag, the pervious vesicle would be capable of containing the tablet or bag until the table disintegrated to less than one tenth of its original size, or until at 90% of the composition in the bag had been dispersed in the water flowing through the pervious vesicle.

In embodiments of the invention, the pervious vesicle may be semi-spherical such that the table may be placed in the vesicle, and the vesicle placed over the hair and subjected to a flowing source of water to produce the dose of water dispersed hair modifier. The water dispersed hair modifier would flow from the pervious vesicle onto the hair, thereby modifying the colour or condition of the hair.

Desirably, the continuous does of water is supplied through a pervious vesicle that is a showerhead, wherein the water dispersible composition may be contained and exposed to the flowing source of water, such that the water dispersed hair colour or condition modifier can flow out of the showerhead and onto hair.

In alternative embodiments of the method of modifying the colour of hair, the water dispersible composition may be added to a dose of water to produce the dose of water dispersed hair colour modifier, and then this dose is applied to the hair as a flowing source of water dispersed hair colour modifier.

Without wishing to be bound by theory, it is proposed that the molecules of colour or condition modifiers, when applied during the method of the invention as a dose of water dispersed colour modifier, are physically forced onto hair during the application of the dose, facilitating their activity.

In some embodiments of the method of modifying the colour of hair, the dose of water dispersed hair colour modifier is applied to the hair after the application of an alkalising and/or neutralising substance that may assist in the modification of the hair colour by opening up the cuticles of the hair shaft. The substance may be any substance that raises the pH of the water it is dispersed in. The substance may, for example, be a pre-colour cleanser, shampoo, rinse and/or spray.

In other embodiments of the method of modifying the colour of hair, after the dose of water dispersed hair colour modifier is applied to the hair, an acidifying substance is applied to the hair to assist in the modification of the hair colour by closing the cuticles of the hair shaft. The substance may be any substance that lowers the pH of the water it is dispersed in. The substance may, for example, be a post-colour cleanser, shampoo, rinse and/or spray.

In other embodiments of the method of modifying the colour of hair, the dose of water dispersed hair colour modifier is applied to the hair after the application of a water-dispersed alkalising/neutralising substance that may assist in the modification of the hair colour by opening up the cuticles of the hair shaft, and then the after the dose of water dispersed hair colour modifier is applied to the hair, a water-dispersed acidifying substance is applied to the hair to assist in the modification of the hair colour by closing the cuticles of the hair shaft.

Water Dispersible Compositions

According to a second aspect, the present invention provides a water dispersible composition comprising a hair modifier, a thickening agent, and a rheology modifier. In embodiments where the composition is in the form of a water disintegratable tablet, the tablet may be a solid, waxy tablet.

In embodiments of the invention, the water dispersible composition is a hair colour modifying composition used to modify the colour of hair for cosmetic purposes, comprising a hair modifier that is a colour modifier, a thickening agent and a rheology modifier. In further embodiments of the invention, the water dispersible composition is a hair condition modifying composition used to modify the condition of hair for cosmetic purposes, comprising a hair modifier that is an oil, a thickening agent and a rheology modifier.

The colour modifier may be any dye, pigment and/or agent capable of modifying the colour of a strand of hair. The modification of the colour of the strand of hair may be by the removal or addition of natural or artificial colour from the cuticle layer of the hair shaft or the cortex layer of the hair shaft.

The colour of the strand of hair may be modified permanently, demi/semi-permanently or temporarily. For example, the modification of the colour of the hair strand may last 1-2 washes, 1-6 washes, 5-10 washes, 6-15 washes, 10-20 washes, or may be effectively permanent such that the alteration of the colour of the strand of hair is only negated by removing (cutting) the hair, or by applying a further colour modifying agent to add or remove colour from the strand of hair or by other environmental or lifestyle factor such as sunlight, salt water and/or chlorinated water. By "washes" is meant a hair cleansing process, generally involving conventional shampoos.

Modifying the colour of the hair also encompasses the removal of colour, such as, for example, the removal of natural or artificial colour from the cuticle or cortex layer of the hair shaft by agents such as ammonia (often used in a process known as "lifting" colour) and hydrogen peroxide (often used to "lighten" or "bleach" hair more than 5 levels), or the removal of deposited colour from the cuticle layer or cortex layer of the hair shaft (often referred to as "stripping" of colour). Modifying the colour of the hair also encompasses the addition of colour to the cortex or cuticle layer of the hair shaft with dyes and pigments.

Accordingly, the colour modifier in the water dispersible compositions of the present invention may be a lifting agent, a bleaching agent, a stripping agent, a dye or a pigment, and many of these agents, dyes and pigments can be identified by an INCI (International Nomenclature of Cosmetic Ingredients) descriptor. It would be understood that none of the below lists of colour modifiers will be exhaustive. As new agents, dyes and pigments are developed and made commercially available, their use in the compositions of the present invention will be assumed and understood to be encompassed by the scope of the invention.

It would be understood that, in general, dyes rely on coloured chemicals or colour modifying chemicals that tend to be in liquid form or are soluble, while pigments are insoluble materials that are generally provided as powders or suspensions of finely ground coloured particles.

The pigments used in the water dispersible compositions are suitable for use in a method of modifying the colour of hair using a dose of water dispersed colour modifier from said water dispersible compositions.

The pigments may be any organic or inorganic pigment(s) selected from the group consisting of animal-derived pigments, metal-derived pigments and plant-derived pigments, such as henna (lawsone), alizarin, polycyclic pigments, azo-pigments, dioxazine pigments, manganese violet, phthalocyanine and quinacridone, lakes, ultramirines, or metal oxides (i.e., iron oxides, chromium oxides and titanium oxides), such as umbers, ochres, siennas, cadmium yellow and cobalt blue.

In general, pigments need to mixed with binders or vehicles, such as water, glycerine and/or alcohol, to assist in the attachment of the pigment to the cuticles of the hair shaft. The pigments may be naturally occurring or synthetic, and have a range of properties that allow them to colour or stain the hair. Many pigments will colour or stain the hair via interactions with proteins or protein side-chains on the cuticle of the hair shaft. Depending on the binder or vehicle used with the pigment, the colour or stain on the hair may last 1-2 washes, 1-3 washes, 2-4 washes, 3-6 washes or up to 10 washes with a conventional hair cleanser (i.e. shampoo).

The compositions of the present invention, when used to modify the colour of the hair, may comprise compatible mixtures of pigments and the compositions may comprise a total of 0.001%-95% (w/w) pigment.

The dyes used in the water dispersible compositions are suitable for use in a method of modifying the colour of hair using a dose of water dispersed colour modifier from said water dispersible compositions.

It would be understood that dyes used in modifying the colour of hair are classified according to the colour resistance, and the dyes used in the water dispersible compositions of the invention may be temporary, semi-permanent, demi-permanent or permanent. The dyes used in the water dispersible compositions of the invention may be non-oxidative or oxidative dyes. The colour results and permanence of the colour may be influenced by the colour of the hair being dyed.

In general, temporary and semi-permanent dyes are non-oxidative dyes (sometimes referred to as direct dyes, though it should be noted that chemicals that may be deemed "direct dyes" may also be used to make permanent dyes) and rely on the deposition of coloured molecules on the cuticle of the hair shaft, with the potential for some penetration to the cortex of the hair shaft. The temporary dyes may also be referred to as acid dyes or anionic dyes. The semi-permanent dyes may be separated into two further groups and referred to as basic dyes/cationic dyes, and nitro aniline/non-ionic dyes. The temporary and semi-permanent dyes may last may last 1-2 washes, 1-3 washes, 2-4 washes, 3-6 washes or up to 10 washes with a conventional hair cleanser, depending on the amount of dyes used in the composition of the invention, and the colour of the hair being modified (i.e., modifying the colour of already bleached, white or blonde hair with a temporary or semi-permanent dye using the methods and compositions of the invention may result in longer lasting colour modification).

The compositions of the invention may comprise one of more direct dye selected from the group consisting of Acid Yellow 23, Acid Orange 7, Acid Yellow 1, Acid Yellow 3, Curry Red, Acid Red 18, Acid Red 52, Acid Red 33, Acid Red 92, Acid Violet 43, Acid Blue 9, Acid Green 25, Acid Black 1, Basic Brown 16, Basic Red 76, Basic Red 2, Basic Red 18, Basic Red 22, Basic Red 46, Basic Yellow 57, Basic Yellow 11, Basic Yellow 28, Basic Yellow 51, Basic Yellow 87, Basic Red 51, Basic Green 4, Basic Brown 17, Basic Blue 99, Basic Blue 3, Basic Blue 7, Basic Blue 9, Basic Blue 26, Basic Blue 41, Basic Orange 31, Basic Orange 1, Basic Orange 2, Basic Violet 2, Basic Violet 1, Basic Violet 4, Basic Violet 14, Basic Violet 16, Basic Violet 35, Basic Violet 11.1, HC Yellow 2, HC Red 3, 2-nitro-p-phenylenediamine, 4-nitro-o-phenylenediamine, HC Yellow 4, HC Blue 1, HC Blue 2, HC Blue 15, HC Red 1, and HC Orange 1.

The temporary dyes used in the compositions of the invention may be any dyes selected from the group consisting of Acid Yellow 23, Acid Orange 7, Acid Yellow 1, Acid Yellow 3, Curry Red, Acid Red 18, Acid Red 52, Acid Red 33, Acid Red 92, Acid Violet 43, Acid Blue 9, Acid Green 25 and Acid Black 1.

The composition may comprise combinations of two or more temporary dyes to achieve the desired colour.

The semi-permanent dyes used in the compositions of the invention may be any dyes selected from the group of basic dyes consisting of Basic Brown 16, Basic Red 76, Basic Yellow 57, Basic Red 51, Basic Brown 17 and Basic Blue 99. The semi-permanent dyes used in the compositions of the invention may be any dyes selected from the group of nitro aniline dyes consisting of HC Yellow 2, HC Red 3, 2-nitro-p-phenylenediamine, 4-nitro-o-phenylenediamine, HC Yellow 4, HC Blue 1, HC Red 1 and HC Orange 1.

The composition may comprise combinations of two or more semi-permanent dyes to achieve the desired colour. The two or more semi-permanent dyes may be all basic dyes or all nitro aniline dyes, or compatible mixtures of basic dyes and nitro aniline dyes.

The composition may comprise combinations of two or more semi-permanent dyes and/or temporary dyes to achieve the desired colour and desired level of permanency.

The compositions of the present invention, when used to modify the colour of the hair temporarily or semi-permanently, may comprise compatible mixtures of temporary dyes, basic dyes and/or nitro aniline dyes. The compositions may comprise a total of 0.001%-95% temporary or semi-permanent dye.

In general, demi-permanent and permanent dyes (known as oxidative dyes) rely on colour precursor molecules that require development with an oxidising agent at a (typically) alkaline pH. The oxidative dyes tend to penetrate the cortex of the hair shaft, as it is proposed that the alkaline pH of the oxidative dyes promotes the temporary swelling/opening of the cuticle layer of the hair shaft, allowing molecules to pass through to the cortex of the hair shaft. The oxidative dyes are generally mixtures of different components that react together at alkaline pH to produce the desired colour and permanency. The resulting colour molecules are then trapped (in part, due to their larger size) in the cortex of the hair shaft, resulting in a demi-permanent or permanent modification of the colour of the hair. The dyes are commonly mixtures of one or more primary intermediate(s) (often p-diamines and/or p-aminophenols; also known as oxidation bases), an oxidising and/or alkylating agent, and one or more coupling agents (also known as colour couplers or reaction modifiers).

The demi-permanent dyes mainly differ from the permanent dyes in the alkylating agent used, in that demi-permanent dyes often do not include ammonia and are less permanent. The demi-permanent dyes may last may last more than 3-6 washes or more than 10 washes with a conventional hair cleanser, depending on the amount of dyes used in the composition of the invention, and the colour of the hair being modified (i.e., modifying the colour of already bleached, white or blonde hair with a demi-permanent dye using the methods and compositions of the invention may result in longer lasting colour modification).

The demi-permanent and permanent dyes used in the compositions of the invention may comprise any primary intermediate selected from the group consisting of 4-amino-m-cresol, 1-hydroxyethyl-4-5-diaminophyrazole sulfate, N,N, Bis [2-hydroxyethyl]-p-phenylene-di-amine sulfate, Hydroxyethyl-p-phenylene-di-amine sulfate, p-amino phenol, p-methyl amino phenol sulphate, p-phenylenediamine sulfate, Tetra amino pyrimidine sulfate and Toluene-2-5-diamine sulfate The demi-permanent and permanent dyes may comprise combinations of two or more primary intermediates to achieve the desired colour and level of permanency.

The demi-permanent and permanent dyes used in the compositions of the invention may comprise any coupling agent selected from the group consisting of Resorcinol, 2-amino-3-hydroxypyridine, 4-amino-2-hydroxytoluene, 2-methyl-5-hydroxyethylaminophenol, 2-methyl resorcinol, 5-amino-6-chloro-o-cresol, 2-amino-4-hydroxyethylamino anisole sulfate, 1-napthol, 2,4,diaminophenoxy ethanol sulfate, m-amino phenol, Phenyl methyl pyrazolone and 4-chloro resorcinol.

The demi-permanent and permanent dyes may comprise combinations of two or more coupling agents to achieve the desired colour and level of permanency.

The demi-permanent and permanent dyes used in the compositions of the invention may comprise any alkylating agent and/or oxidising agent, either alone or in combination, required to achieve the desired level of colour and permanency. A common oxidising agent is hydrogen peroxide, though the use of a dose of water and oxygen in the atmospheric air may be sufficient to act as an oxidising agent in a demi-permanent or permanent dye in a composition used during the method of the present invention. It would be understood that the oxidising agent is also generally responsible for the lightening of the natural hair pigments when using demi-permanent and permanent hair dyes, as the melanin, eumelanin and pheomelanin in the hair shaft lose colour when oxidised.

Non-limiting examples of alkylating agents include ammonia, ethanolamine or any compatible agent that can achieve an appropriate dye pH to allow for the conversion of the dye precursor molecules to the required colour molecules.

The demi-permanent and permanent dyes used in the compositions of the invention may comprise combinations of one or more primary intermediates and/or one or more coupling agents and/or one or more alkylating and/or oxidising agents to achieve the desired colour and desired level of permanency. The compositions of the present invention, when used to modify the colour of the hair permanently or demi-permanently, may comprise compatible mixtures of primary intermediates, coupling agents, alkylating and/or oxidising agents at individual concentrations suitable to facilitate the colour reactions required to achieve the desired level of colour and permanency. The compositions may comprise a total of 0.001%-95% (w/w) permanent or demi-permanent dye.

The compositions of the present invention, when used to modify the colour of the hair, may comprise compatible mixtures of pigments, temporary dyes, semi-permanent dyes, demi-permanent dyes and/or permanent dyes, and the compositions may comprise a total of 0.001%-95% (w/w) of pigment, temporary dye, semi-permanent dye, demi-permanent dye and/or permanent dye. The combinations and percentages of pigments, temporary dyes, semi-permanent dyes, demi-permanent dyes and/or permanent dyes in the present compositions may be modified and adjusted based on the desired level of permanency, and/or intensity and/or colour profile on the hair of the subject.

The lifting agents used in the water dispersible compositions are suitable for use in a method of modifying the colour of hair using a dose of water dispersed colour modifier from said water dispersible compositions. It would be understood that a lifting agent is generally for the removal of natural colour from the hair shaft resulting in the hair being lightened up to 5 levels. Lifting agents may be used in conjunction with demi-permanent and permanent dyes or alone. The lifting agents may be any agents or compositions capable of lightening the hair by up to 5 levels. The compositions may comprise a total of 0.001%-95% (w/w) lifting agent.

The bleaching agents used in the water dispersible compositions are suitable for use in a method of modifying the colour of hair using a dose of water dispersed colour modifier from said water dispersible compositions. It would be understood that a bleaching agent is generally for the removal of natural colour from the hair shaft resulting in the hair being lightened by more than 5 levels.

The bleaching agents may be any agents or compositions capable of lightening the hair by over 5 levels. The compositions may comprise a total of 0.001%-95% (w/w) bleaching agent.

The stripping agents used in the water dispersible compositions are suitable for use in a method of modifying the colour of hair using a dose of water dispersed colour modifier from said water dispersible compositions. It would be understood that a stripping agent is generally for the removal of artificial colour from the hair shaft resulting in the hair being returned to its natural colour (or close to the natural hair colour) or the colour of the hair prior to the addition of an artificial dye or pigment (or close to the colour of the hair prior to the addition of an artificial dye or pigment).

The stripping agents may be any agents or compositions capable of removal artificial colour from the hair shaft resulting in the hair being returned to its natural colour (or close to the natural hair colour) or the colour of the hair prior to the addition of an artificial dye or pigment (or close to the colour of the hair prior to the addition of an artificial dye or pigment). The compositions may comprise a total of 0.001%-95% (w/w) stripping agent.

It would be understood that the active components and compounds in the lifting, bleaching and stripping agents are similar or the same, wherein the level of colour removal can be manipulated and controlled by using different amounts of active components and compounds.

The compositions of the present invention, when used to modify the colour of the hair, may comprise compatible mixtures of lifting agents, bleaching agents and stripping agents at individual concentrations suitable to facilitate the colour reactions required to achieve the desired level of colour removal. The compositions may comprise a total of 0.001%-95% (w/w) lifting, bleaching and/or stripping agent.

A water dispersible composition of the present invention may only comprise one or more colour modifiers that remove colour from the hair, or may only comprise one or more colour modifiers that add colour to the hair. For example, the composition may comprise a dye and a pigment, or may comprise two different dyes. In another example, the composition may comprise a stripping agent and a bleaching agent.

In another embodiment, a water dispersible composition of the present invention may comprise one or more colour modifiers that remove colour from the hair and one or more colour modifiers that add colour to the hair. For example, the composition may comprise a lifting agent and a dye, or the composition may comprise a stripping agent, a bleaching agent and a pigment, or the composition may a pigment and a dye.

The compositions of the present invention, when used to modify the colour of the hair, may comprise compatible mixtures of pigments, temporary dyes, semi-permanent dyes, demi-permanent dyes, permanent dyes, lifting agents, bleaching agents and/or stripping agents and the compositions may comprise a total of 0.001%-95% (w/w) of pigment, temporary dye, semi-permanent dye, demi-permanent dye, permanent dye, lifting agent, bleaching agent and/or stripping agent. In further embodiments of the invention, the compositions may comprise a total of 0.01%-50% (w/w), 10%-80% (w/w), 0.1%-5% (w/w), 1%-20% (w/w), 6%-8% (w/w), 0.1%-10% (w/w), 0.1%-3% (w/w), 40%-50% (w/w), or 5%-15% (w/w), of pigment, temporary dye, semi-permanent dye, demi-permanent dye, permanent dye, lifting agent, bleaching agent and/or stripping agent.

The colour modifier in the water dispersible compositions of the present invention may comprise other ingredients, chemicals and/or components in addition to the non-exhaustive lists of pigments, dyes, lifting/bleaching/stripping agents included below. These other ingredients, chemicals and/or components may include, but are not limited to, thickeners, film formers, conditioners, cleansers, colour protections agents, solubilizes, surfactants, stabilizers, polymers, bases and texturing agents, all of which would be known in the field.

The rheology modifier used in the compositions of the present invention may be any compound or composition suitable for increasing the viscosity of the fluid components of the compositions during manufacture. The rheology modifier may also increase the viscosity of the fluid components by stabilising oil-in-water and water-in-oil emulsions to aid in the formation of the compositions. By "suitable" is meant that the components in the resulting viscous mixture of components are relatively evenly dispersed, remain active and are resistant to degradation or disintegration (when not exposed to water) over time. The skilled addressee would understand that a rheology modifier is essentially a compound that, when added to mixtures of fluid components or emulsions with low viscosity may increase the viscosity of the mixture of fluid components or emulsion, or at least maintain the viscosity of the emulsion, and generally assist in the maintenance of stable emulsions.

The rheology modifier may comprise inorganic or organic molecules and may generally be added to the mixture of fluid components or emulsion as an aqueous phase. It is preferably an organic molecule, such as an organic polymer. Organic molecules suitable for use in the present invention as rheology modifiers include, but are not limited to, polyacrylates, polyurethanes and polyethers.

In preferred embodiments of the invention, the compositions comprise an organic polymer that is water soluble.

The rheology modifier may also be co-polymer. The skilled addressee would understand that a co-polymer is any polymer comprising more than one type of monomer.

The percentage of each monomer in the co-polymer, as well as the length of any organic polymer for use in the compositions of the present invention, will be dependent on the desired properties of the rheology modifier. It would be understood by the person skilled in the art that the desired properties of the rheology modifier may also be influenced by the properties of other components in the compositions: for example, whether the compositions comprised a UVR filtering agent that was a solid or liquid, and/or whether the protein extracts was oil, water or solvent soluble or miscible, may influence the choice of rheology modifier. Further to this, the total oil content in the compositions may also influence the choice of rheology modifier. The choice of rheology modifier may also be influenced by the required dissolution rate of the particular compositions.

In preferred embodiments of the invention, the rheology modifier is a water-soluble organic polymer selected from the group consisting of acrylates/alkyl acrylate crosspolymers, polyacrylamide, carbomers and polyethylene glycols.

In preferred embodiments, the rheology modifier is a polyethylene glycol or a derivative thereof. In particularly preferred embodiments, the rheology modifier is PEG-4000.

In preferred embodiments of the invention, the compositions may comprise the rheology modifier at a concentration of about 4-70% (w/w). More preferably, the compositions may comprise a rheology modifier at a concentration of about 30-60% (w/w). In further preferred embodiments, the compositions may comprise a rheology modifier at a concentration of about 25%-50% (w/w). In other preferred embodiments, the compositions may comprise a rheology modifier at a concentration of about 25%, 30%, 35%, 40% or 45% (w/w).

In alternative embodiments, the rheology modifier is a glycerine, glycerol ester or a derivative thereof. The glycerol ester may, for example, be glyceryl oleate or glyceryl stearate. It would be understood that the glycerol esters may also behave as anionic emulsifiers.

In particularly preferred embodiments, the compositions of the present invention comprise a polyethylene glycol at a concentration of about 35%-50% (w/w).

In other preferred embodiments of the present invention, the compositions comprise PEG-4000 at a concentration of about 30%, 35%, 40% or 45% (w/w).

In particularly preferred embodiments, the compositions of the present invention comprise a glycerol ester at a concentration of about 10%-20%, 15%-25, 5%-15%, 20%-40%, or 35%-45% (w/w).

In other preferred embodiments of the present invention, the compositions comprise a glycerol ester or a derivative thereof at a concentration of about 5%, 10%, 15%, 20%, 25%, 30%, 35%, 40% or 45% (w/w).

In particularly preferred embodiments, the compositions of the present invention comprise glyceryl stearate or a derivative thereof at a concentration of about 10%-20%, 15%-25, 5%-15%, 20%-40%, or 35%-45% (w/w).

In particularly preferred embodiments, the compositions of the present invention comprise glyceryl oleate or a derivative thereof at a concentration of about 10%-20%, 15%-25, 5%-15%, 20%-40%, or 35%-45% (w/w).

The thickening agent used in the compositions of the present invention may be any compound or composition suitable for sufficiently solidifying the composition such that it may be formed into a solid or semi-solid substance, such as a powder, granulated powder, slurry or paste. The thickening agent may be a non-aqueous phase thickener and may be a carbohydrate-rich, mineral-rich or lipid-rich agent.

The mineral-rich thickening agent may be selected from the group selected from inorganic and/or hydrophilic clays or silicas. Non-limiting examples include bentonite clays, attapulgite clays, organoclays and hectorite clays.

The thickening agent may be a carbohydrate-rich agent such as cellulose, xantham or gelatine. In embodiments of the invention, the thickening agent is arrowroot powder.

More preferably, the thickening agent is a lipid-rich agent. Non-limiting examples of lipid-rich thickening agents include beeswax and hydrogenated castor oil (also known as carbowax, Sabowax ELH 40 and/or PEG-40).

It would be understood that hydrogenated castor oil, being a water-soluble wax, allows for a solid or semi-solid bind of the composition whilst disintegrating quickly in water.

In preferred embodiments of the invention, the compositions may comprise the thickening agent at a concentration of about 1%-15% (w/w). More preferably, the compositions comprise hydrogenated castor oil at a concentration of about 5%-15%, 1%-10%, 1%-5%, 3%-5%, or 1%-3% (w/w). In embodiments of the invention where the composition is in the form of a solid water disintegratable tablet, the amount of thickening agent required may be higher than that required for a semi-solid composition. In preferred embodiments, the compositions may comprise PEG-40 at a concentration of about 1%-5%, 3%-5%, or 1%-3% (w/w).

In an embodiment of the invention, the composition is a water dispersible composition for modifying the colour of the hair, comprising a lipid-rich thickening agent at a concentration of about 1%-5% (w/w), a water soluble, organic rheology modifier at a concentration of about 40%-45% (w/w), and a colour modifier at a concentration of about 1%-20% (w/w).

In another embodiment of the invention, the composition is a water dispersible composition for modifying the colour of the hair, comprising hydrogenated castor oil at a concentration of about 1%-5% (w/w), a glycerol ester at a concentration of about 20%-45% (w/w), and a colour modifier at a concentration of about 0.5%-30% (w/w).

The compositions of the present invention may further comprise an emulsifier. The emulsifier used in the compositions of the present invention may be any compound or composition suitable for producing mixtures of substances that would not ordinarily mix (emulsions). In general, an emulsifier consists of a water-loving hydrophilic head and an oil-loving hydrophobic tail. The emulsifier may be an oil-in-water or water-in-oil emulsifier.

Accordingly, in various embodiments of the invention, the water dispersible composition comprises a colour modifier, a thickening agent, a rheology modifier and an emulsifier. In other embodiments of the invention, the water dispersible composition comprises an oil, a thickening agent, a rheology modifier and an emulsifier.

In embodiments of the present invention, the emulsifier may be an ionic (cationic or anionic) emulsifier, a zwitterionic emulsifier or a non-ionic emulsifier.

Non-limiting examples of cationic emulsifiers suitable for use in the compositions of the present invention include quaternary ammonium compounds such as benzalkonium chloride, benzethonium chloride, stearalkonium chloride and cetrimonium chloride.

It would be understood that the cationic emulsifiers may also serve as an antibacterial agent in view of the known ability of cationic surfactants to disrupt the cell membrane of some microorganisms.

Non-limiting examples of anionic emulsifiers suitable for use in the compositions of the present invention include sodium lauryl sulfate (SLS), sodium lauryl sulfoacetate, sodium cocoyl isethionate, ammonium lauryl sulfate (ALS), or their ethoxylated companions, sodium laureth sulfate (SLES), sodium docusate, the taurates, the isethionates, the olefin sulfonates, and the sulfosuccinates.

Non-limiting examples of zwitterionic emulsifiers suitable for use in the compositions of the present invention include sodium lauriminodipropionate and Disodium lauroamphodiacetate.

Non-limiting examples of nonionic emulsifiers suitable for use in the compositions of the present invention include sorbitan esters and polyoxyethelene derivatives of sorbitan esters such as the Tweens (polysorbate), long chain (fatty) alcohols such as cetyl alcohol, cetearyl alcohol, lauryl alcohol, oleyl alcohol, stearyl alcohol, polyoxyethylene ethers of fatty alcohols, such as ceteareth, ceteth, oleth, steareth and laureth, the fatty alcohol ethoxylates, fatty alcohol alkoxylates, and nonylphenyl ethoxylates.

The compositions may comprise one or more emulsifiers that is/are a nonionic emulsifier selected from the group consisting of a cetearyl alcohol, a ceteareth, a Tween emulsifier, an alcohol alkoxylate, an alcohol ethoxylate and a nonylphenyl ethoxylate.

In preferred embodiments of the invention, the compositions comprise the non-ionic emulsifier known as Emulgade® 1000NI (BASF), which comprises cetearyl alcohol and ceteareth-20.

In preferred embodiments of the invention, the compositions comprise the alcohol alkoxylate known as TERIC BL8® (Huntsman).

In preferred embodiments of the invention, the compositions comprise the alcohol ethoxylate known as TERIC 16A30® (Huntsman).

In preferred embodiments of the invention, the compositions comprise a nonylphenyl ethoxylate known as TERIC N9® or TERIC N5® (Huntsman).

In preferred embodiments of the invention, the compositions comprise the non-ionic emulsifier known as Eumulgin® B3 (BASF), which comprises ceteareth-30.

In preferred embodiments of the invention, the compositions comprise the non-ionic emulsifier, Tween-80.

In preferred embodiments of the invention, the compositions comprise the cationic emulsifier, cetrimonium chloride.

In preferred embodiments of the present invention, the compositions may comprise two or more different emulsifiers. The two or more different emulsifiers may be different non-ionic emulsifiers, or different anionic emulsifiers, or different cationic emulsifiers, or different zwitterionic emulsifiers or a combination of non-ionic, anionic, cationic and/or zwitterionic emulsifiers.

In preferred embodiments of the invention, the compositions comprise two different types of emulsifiers. In more preferred embodiments of the inventions, the two types emulsifiers are non-ionic emulsifiers and cationic emulsifiers.

In particularly preferred embodiments of the invention, the compositions comprise at least one cationic emulsifier and at least two different non-ionic emulsifiers. In further preferred embodiments of the invention, the compositions comprise one cationic emulsifier and at least three different non-ionic emulsifiers. The compositions may comprise at least four different non-ionic emulsifiers.

In preferred embodiments, the compositions comprise at least three emulsifiers selected from the group consisting of a cetearyl alcohol, a ceteareth, a Tween emulsifier, a nonylphenyl ethoxylate, an alcohol alkoxylate, an alcohol ethoxylate and a quaternary ammonium compound.

In preferred embodiments, the compositions comprise at least four emulsifiers selected from the group consisting of a cetearyl alcohol, a ceteareth, a Tween emulsifier, a nonylphenyl ethoxylate, an alcohol ethoxylate, an alcohol alkoxylate, and a quaternary ammonium compound.

In preferred embodiments, the compositions comprise at least three emulsifiers selected from the group consisting of cetearyl alcohol, ceteareth-20, ceteareth-30, Tween-80, TERIC® N5, TERIC® N9, TERIC® BL8, TERIC® 16A30 and Cetrimonium chloride.

In embodiments of the invention, the total concentration of emulsifier in the compositions is about 10%-40% or 10%-20% (w/w).

In preferred embodiments, the compositions comprise Emulgade® 1000NI at a concentration of about 1%-20% or about 5%-15% or about 1%-10% (w/w). In preferred embodiments of the invention, the compositions may comprise Emulgade® 1000NI at a concentration of about 1%-5% (w/w).

In preferred embodiments, the compositions comprise Eumulgin® B3 at a concentration of about 1%-20% or about 5%-15% or about 1%-10% or about 1%-5% (w/w). In preferred embodiments of the invention, the compositions may comprise Eumulgin® B3 at a concentration of about 1%-3% (w/w).

In embodiments of the invention, the total concentration of cationic emulsifier in the compositions is about 1%-15% (w/w). In preferred embodiments, the total concentration of cationic emulsifier in the compositions is about 4%-6%, 5%-7%, 6%-8%, 7%-8%, 5%-10%, 8%-12%, or 10%-15% (w/w).

In preferred embodiments, the cationic emulsifier in the compositions is cetrimonium chloride and is present at a concentration of about 4%-5, 5%-6%, 6%-7%, 7%-8%, 8%-9%, 9%-10%, 10%-11%, 9%-12%, 10%-15%, or 14%-18% (w/w).

In embodiments of the invention, the total concentration of non-ionic emulsifier in the compositions is about 5%-30% (w/w). In preferred embodiments, the total concentration of non-ionic emulsifier in the compositions is about 10%-20% or 10%-15% (w/w).

In preferred embodiments, the compositions comprise cetearyl alcohol at a concentration of about 1%-5% (w/w). In preferred embodiments of the invention, the compositions may comprise cetearyl alcohol at a concentration of about 1%-3% (w/w).

In preferred embodiments, the compositions comprise ceteareth-20 and/or ceteareth-30 at a concentration of about 1%-10% (w/w). In preferred embodiments of the invention, the compositions may comprise cetearyl alcohol at a concentration of about 2%-5% (w/w).

In preferred embodiments, the compositions comprise a Tween emulsifier at a concentration of about 1%-10% (w/w). In preferred embodiments of the invention, the compositions may comprise a Tween emulsifier at a concentration of about 4%-7% (w/w).

In preferred embodiments, the compositions comprise alcohol alkoxylate at a concentration of about 1%-10% (w/w). In preferred embodiments of the invention, the compositions may comprise alcohol alkoxylate at a concentration of about 4%-7% (w/w).

In preferred embodiments, the compositions comprise alcohol ethoxylate at a concentration of about 1%-15% (w/w). In preferred embodiments of the invention, the compositions may comprise alcohol ethoxylate at a concentration of about 5%-10%, 4%-8% or 5%-7% (w/w).

In preferred embodiments, the compositions comprise nonylphenyl ethoxylate at a concentration of about 0.2%-10% (w/w). In preferred embodiments of the invention, the compositions comprise nonylphenyl ethoxylate at a concentration of about 0.5%-3%, 3%-7% (w/w).

In very preferred embodiments of the invention, the compositions may comprise at least two emulsifiers selected from the group consisting of Emulgade® 1000NI at a concentration of about 1%-10% (w/w), cetrimonium chloride at a concentration of about 5%-15% (w/w), Tween-80 at a concentration of about 4%-6% (w/w), TERIC® N5 at a concentration of about 3%-6% (w/w), TERIC® N9 at a concentration of about 0.5%-2% (w/w), Eumulgin® B3 at a concentration of about 1%-5% (w/w) and TERIC® BL8 at a concentration of about 4%-6% (w/w).

In very preferred embodiments of the invention, the compositions may comprise at least two emulsifiers selected from the group consisting of Emulgade® 1000NI at a concentration of about 3%-5% (w/w), cetrimonium chloride at a concentration of about 6%-12% (w/w), TERIC® N9 at a concentration of about 0.5%-2% (w/w), Eumulgin® B3 at a concentration of about 4%-6% (w/w), and TERIC® 16A30® at a concentration of about 4%-6% (w/w).

The oil may be any oil suitable for use with hair, and may be any mixture of any number of different oils. In preferred embodiments, the compositions may comprise at least 2%, at least 5%, at least 10%, at least 15%, at least 20%, or at least 30% (w/w) oil.

The oil in the compositions of the present invention may be any oil derived from any oil-producing plant, and may be any mixture of any number of different plant oils. In preferred embodiments, the compositions may comprise at least 2%, at least 5%, at least 10%, at least 15%, at least 20%, at least 25%, or at least 30% (w/w) plant oil.

In preferred embodiments, the compositions may comprise about 15%-20%, 15%-25%, 20%-25% or 25%-35% (w/w) plant oil.

The plant oils used may be oils that have natural moisturising properties. In preferred embodiments of the invention, the total plant oil comprises at least one other plant oil selected from the group consisting of coconut oil, shea oil/butter, olive oil, almond oil, peppermint oil, apricot kernel oil, tulsi oil, lemon grass oil, lavender oil, sunflower seed oil, wheat germ oil, argan oil, camellia oil, castor seed oil, macadamia oil, meadowfoam seed oil, hemp seed oil, jojoba oil, grape seed oil, marula oil, rice bran oil, avocado oil, raspberry seed oil, citrus oil and carrot seed oil.

In embodiments of the invention, the compositions comprise coconut oil. In particularly preferred embodiments of the invention, the compositions may comprise up to 20% (w/w) coconut oil. In preferred embodiments, the compositions may comprise at least 2%, at least 5%, at least 7%, or at least 10% (w/w) coconut oil. In other preferred embodiments, the compositions may comprise about 1%-5% or 3%-5% (w/w) coconut oil.

In preferred embodiments of the invention, in addition to the coconut oil, the total plant oil comprises at least one oil selected from the group consisting of macadamia oil, shea oil/butter, olive oil, peppermint oil, wheat germ oil, marula oil, argan oil, camellia oil, castor seed oil, jojoba oil, raspberry seed oil, and carrot seed oil.

In another embodiment of the invention, the composition is a water dispersible composition for modifying the condition of the hair, comprising one or more emulsifiers at a concentration of about 10%-40% (w/w), a lipid-rich thickening agent at a concentration of about 1%-15% (w/w), one or more plant oils at a concentration of about 15%-25% (w/w), and a water soluble, organic rheology modifier at a concentration of about 30%-45% (w/w).

In further preferred embodiments of the invention, the composition is a water dispersible composition for modifying the condition of the hair, comprising one or more cationic and/or non-ionic emulsifiers at a concentration of about 10%-20% (w/w), a lipid-rich thickening agent at a concentration of about 1%-5% (w/w), one or more plant oils at a concentration of about 15%-25% (w/w), and a water soluble, organic rheology modifier at a concentration of about 40%-45% (w/w).

In a preferred embodiment of the invention, the composition is a water dispersible composition for modifying the condition of the hair, comprising one or more cationic and/or non-ionic emulsifiers at a concentration of about 10%-20% (w/w), hydrogenated castor oil at a concentration of about 1%-5% (w/w), one or more plant oils at a concentration of about 15%-25% (w/w), and a glycerol ester at a concentration of about 20%-45% (w/w).

In embodiments of the invention, the colour modifying compositions also comprise an oil as described herein. Accordingly, in one embodiment of the invention, the composition is a water dispersible composition for modifying the colour of the hair, comprising a lipid-rich thickening agent at a concentration of about 1%-15% (w/w), one or more plant oils at a concentration of about 15%-25% (w/w), a water soluble, organic rheology modifier at a concentration of about 30%-45% (w/w), and a colour modifier at a concentration of about 5%-50% (w/w).

In embodiments of the invention, the colour modifying compositions also comprise an oil as described herein. Accordingly, in one embodiment of the invention, the composition is a water dispersible composition for modifying the colour of the hair, comprising a lipid-rich thickening agent at a concentration of about 1%-5% (w/w), one or more plant oils at a concentration of about 25%-35% (w/w), a water soluble, organic rheology modifier at a concentration of about 30%-45% (w/w), and a colour modifier at a concentration of about 0.5%-10% (w/w).

In a preferred embodiment of the invention, the composition is a water dispersible composition for modifying the colour of the hair, comprising one or more emulsifiers at a total concentration of about 10%-20% (w/w), a lipid-rich thickening agent at a concentration of about 1%-5% (w/w), a water soluble, organic rheology modifier at a concentration of about 40%-45% (w/w), and a colour modifier at a concentration of about 1%-20% (w/w).

In a preferred embodiment of the invention, the composition is a water dispersible composition for modifying the colour of the hair, comprising one or more cationic and/or non-ionic emulsifiers at a total concentration of about 10%-20% (w/w), hydrogenated castor oil at a concentration of about 1%-5% (w/w), one or more plant oils at a concentration of about 15%-35% (w/w), a polyethylene glycol at a concentration of about 20%-45% (w/w), and a colour modifier at a concentration of about 0.5%-30% (w/w).

It would be understood by the person skilled in the art that the compositions of the invention can also include preservatives, antiseptics, emollients, protein extracts, ultraviolet radiation (UVR) filtering agents, fragrance, active agents, excipients, diluents and colouring agents.

The emollient used in the composition of the present invention may be any compound or composition that may assist in forming an at least partially waterproof layer on a hair shaft that may assist in the prevention of evaporation of water from the hair shaft. The emollient may be a lipid-based or silicone-based emollient. In embodiments of the present compositions, there is comprised 0.5%-5% (w/w) emollient. In embodiments, the compositions may comprise coconut oil, or derivatives thereof, that serve as an emollient. A common example of a coconut oil derived emollient is cetiol C5. In other embodiments of the invention, the compositions may also comprise charged polymers, and in particular, cationic polymers such as polyquaternium polymers, that may serve a similar purpose to conventional emollients by forming a hydrophobic layer on the hair shaft.

The protein extract may be any extract comprising proteins, peptides and/or amino acids that are suitable for use on the hair and may assist worth the strengthening of the hair shaft.

The protein extract may be any hydrolysed protein extracts, silk-based protein extracts, plant-based protein extracts, including but not limited to such as hydrolysed silk, keratin, wheat protein, collagen and soy protein. In embodiments of the present compositions, there is comprised 0.5%-5% (w/w) protein extract.

The preservative used in the tables of the present invention may be any substance that assists in the prevention of microbial growth and degradation of the composition.

The preservative may be an anti-microbial or an anti-oxidant. In preferred embodiments of the invention, the compositions may comprise a preservative at a concentration of 0.5%-5% (w/w). More preferably, the compositions may comprise a preservative at a concentration of 1%-3% (w/w).

The UVR filtering agent used in the compositions of the present invention may be any compound that has the capacity to absorb, block or reflect UVR, wherein the UVR occurs at a wavelength within the range of about 280 nm to about 400 nm. It would be understood by the person skilled in the art that this wavelength range encompasses both the UVA and UVB wavelength range.

The UVR filtering agent may predominantly absorb, block or reflect UVA or UVB, or it may be a broad spectrum UVR filtering agent that absorbs, blocks or reflects UVR occurring at wavelengths that fall within both the UVA and UVB ranges.

The UVR filtering agent may be a chemical sunscreening agent or a physical sunscreening agent. The choice of UVR filtering agent or agents used in the compositions would be influenced by factors such as safety and regulatory considerations, whether the agents were liquid or solid, and the capability of the UVR filtering agent(s) to be combined with the other components to form a water-soluble cosmetic composition.

Definitions

In the context of the present invention, the words "comprise", "comprising" and the like are to be construed in their inclusive, as opposed to their exclusive, sense, that is in the sense of "including, but not limited to".

PREFERRED EMBODIMENTS OF THE INVENTION

The present invention will now be described with reference to the following examples which should be considered in all respects as illustrative and non-restrictive. Examples of suitable formulations for the cleansing and treatment compositions are set out below, together with details of recommended treatment procedures using the shower head and compositions of the invention.

Compositions for Modifying the Hair

An example of a colour modifying water dispersible composition for use with a flowing source of water of the present invention comprises 12-13% (w/w) emulsifier, 40-45% (w/w) rheology modifier, 2.5-3% (w/w) thickening agent, 15-25% (w/w) oil, and 6-8% (w/w/) colour modifier, wherein the colour modifier is a semi-permanent dye, and the composition is pressed into a semi-solid, water disintegratable table.

Another example of a colour modifying water dispersible composition for use with a flowing source of water of the present invention comprises 10-15% (w/w) emulsifier, 40-45% (w/w) rheology modifier, 2.5-3% (w/w) thickening agent, 15-25% (w/w) oil, and 0.1-3% (w/w/) colour modifier, wherein the colour modifier is a semi-permanent or demi-permanent dye, or a combination thereof, and the composition is pressed into a semi-solid, water disintegratable table.

In a further example of a preferred embodiment of a colour modifying water dispersible composition for use with a flowing source of water of the present invention comprises 4.5% (w/w) Emulgade® 1000NI, about 44% (w/w) PEG-4000, about 4% (w/w) coconut oil or cetiol-C5, about 2.5% (w/w) hydrogenated castor oil, about 3% (w/w) non-ionic surfactant, and about 24% (w/w) plant oil, wherein the tablets comprises about 3% (w/w) argan oil, and 0.1-3% (w/w/) direct dye, wherein the direct dye is a semi-permanent dye, demi-permanent dye, or temporary dye, a combination thereof, and the composition is pressed into a semi-solid, water disintegratable table.

An example of a colour modifying water dispersible composition for use with a flowing source of water of the present invention comprises 12-13% (w/w) emulsifier, 40-45% (w/w) rheology modifier, 2.5-3% (w/w) thickening agent, 20-30% (w/w) oil, and 6-8% (w/w/) colour modifier, wherein the colour modifier is a semi-permanent dye, and the composition is pressed into a semi-solid, water disintegratable table.

Another example of a preferred embodiment of a colour modifying water dispersible composition for use with a flowing source of water of the present invention comprises 14-18% (w/w) emulsifier, 40-45% (w/w) rheology modifier, 2.5-3% (w/w) thickening agent, about 25% (w/w) plant oil, and 0.1-3% (w/w/) colour modifier, wherein the colour modifier is a semi-permanent or demi-permanent dye, or a combination thereof, and the composition is pressed into a semi-solid, water disintegratable table.

Another example of a colour modifying water dispersible composition for use with a flowing source of water of the present invention comprises 14-18% (w/w) emulsifier, 40-45% (w/w) rheology modifier, 2.5-3% (w/w) thickening agent, about 25% (w/w) plant oil, and 0.1-3% (w/w/) colour modifier, wherein the colour modifier is a permanent, semi-permanent or demi-permanent dye, or a combination thereof, and the composition is prepared as a granulated substance for use in a porous bag.

A further example of a colour modifying water dispersible composition for use with a flowing source of water of the present invention comprises 4.5% (w/w) Emulgade® 1000NI, about 44% (w/w) PEG-4000, about 4% (w/w) coconut oil, about 2.5% (w/w) hydrogenated castor oil, about 3% (w/w) non-ionic surfactant, about 10% (w/w) cationic surfactant, and about 25% (w/w) plant oil, wherein the plant oil comprises at least olive oil and/or castor oil and/or argan oil and 1-2% (w/w) total direct dye, wherein the direct dye is a semi-permanent dye, demi-permanent dye, or temporary dye, a combination thereof, and the composition is prepared as a powder or granulated substance for use in a porous bag.

Another example of a colour modifying water dispersible composition for use with a flowing source of water of the present invention comprises 4.5% (w/w) Emulgade® 1000NI, about 44% (w/w) PEG-4000, about 2.5% (w/w) SABOWAX ELH 40, and about 25%-35% (w/w) total plant oil, about 10% (w/w) cetrimonium chloride, about 4% (w/w) coconut oil or cetiol C5, about 3% (w/w) Eumulgin® B3, and 0.1-3% (w/w) direct dye, wherein the direct dye is a semi-permanent dye, demi-permanent dye, or temporary dye, a combination thereof, and the composition is pressed into a semi-solid, water disintegratable table.

Yet another example of a colour modifying water dispersible composition for use with a flowing source of water of the present invention comprises 4.5% (w/w) Emulgade® 1000NI, about 44% (w/w) PEG-4000, about 2.5% (w/w) PEG-40, and about 25%-35% (w/w) total plant oil, about 10% (w/w) cetrimonium chloride, about 4% (w/w) coconut oil or cetiol C5, about 3% (w/w) Eumulgin® B3, and 1-2% (w/w) colour modifier, and the composition is prepared as a powder or granulated substance for use in a porous bag.

Another example of a colour modifying water dispersible composition for use with a flowing source of water of the present invention comprises 4.5% (w/w) Emulgade® 1000NI, about 44% (w/w) PEG-4000, about 2.5% (w/w) PEG-40, and about 25%-35% (w/w) total plant oil, about 10% (w/w) cetrimonium chloride, about 4% (w/w) coconut oil or cetiol C5, about 3% (w/w) Eumulgin® B3, about 2% (w/w) protein, and 0.1-3% (w/w) dye or pigment, wherein the dye or pigment is a permanent, semi-permanent, demi-permanent, or temporary dye or pigment, a combination thereof, and the composition is pressed into a semi-solid, water disintegratable table.

Another example of a colour modifying water dispersible composition for use with a flowing source of water of the present invention comprises 4.5% (w/w) cetearyl alcohol and ceteareth-20, about 44% (w/w) PEG-4000, about 2.5% (w/w) hydrogenated castor oil, and about 15%-25% (w/w) total plant oil, about 10% (w/w) cetrimonium chloride, about 4% (w/w) coconut oil or cetiol C5, about 3% (w/w) ceteareth, about 2% (w/w) protein, and 2-7% (w/w/) dye or pigment, wherein the dye or pigment is a permanent, semi-permanent, demi-permanent, or temporary dye or pigment, a combination thereof, and the composition is pressed into a semi-solid, water disintegratable table.

Another example of a colour modifying water dispersible composition for use with a flowing source of water of the present invention comprises 4.5% (w/w) Emulgade® 1000NI, about 44% (w/w) PEG-4000, about 2.5% (w/w) SABOWAX ELH 40, and about 25%-35% (w/w) total plant oil, about 10% (w/w) cetrimonium chloride, about 4% (w/w/) coconut oil or cetiol C5, about 3% (w/w) Eumulgin® B3, about 2% (w/w) protein, and about 0.5% (w/w) basic red 51 direct dye, 0.18% (w/w) basic blue 124 direct dye, and 1% (w/w) basic yellow 87 direct dye, and the composition is prepared as a powder or granulated substance for use in a porous bag.

Another example of a colour modifying water dispersible composition for use with a flowing source of water of the present invention comprises 4.5% (w/w) Emulgade® 1000NI, about 44% (w/w) PEG-4000, about 2.5% (w/w) hydrogenated castor oil, and about 25%-35% (w/w) total plant oil, about 10% (w/w) cetrimonium chloride, about 4% (w/w/) coconut oil or cetiol C5, about 3% (w/w) Eumulgin® B3, about 2% (w/w) protein, and about 0.5% (w/w) basic red 51 direct dye, 0.18% (w/w) basic blue 124 direct dye, and 1% (w/w) basic yellow 87 direct dye, and the composition is pressed into a semi-solid, water disintegratable table.

A further example of a colour modifying water dispersible composition for use with a flowing source of water of the present invention comprises 4.5% (w/w) cetearyl alcohol and ceteareth-20, about 44% (w/w) PEG-4000, about 2.5% (w/w) hydrogenated castor oil, and about 15%-25% (w/w) total plant oil, about 10% (w/w) cetrimonium chloride, about 4% (w/w/) coconut oil or cetiol C5, about 3% (w/w) ceteareth-30, about 2.5% (w/w) protein, and about 2.5% (w/w) basic orange 31 direct dye, 0.15% (w/w) basic violet 2 direct dye, 3% (w/w) basic yellow 87 direct dye, and 1.5% (w/w) basic red 51 direct dye, and the composition is prepared as a powder or granulated substance for use in a porous bag.

Another example of a colour modifying water dispersible composition for use with a flowing source of water of the present invention comprises 4.5% (w/w) cetearyl alcohol and ceteareth-20, about 44% (w/w) PEG-4000, about 2.5% (w/w) hydrogenated castor oil, and about 15%-25% (w/w) total plant oil, about 10% (w/w) cetrimonium chloride, about 4% (w/w/) coconut oil or cetiol C5, about 3% (w/w) ceteareth-30, about 2.5% (w/w) protein, and about 2.5% (w/w) basic orange 31 direct dye, 0.15% (w/w) basic violet 2 direct dye, 3% (w/w) basic yellow 87 direct dye, and 1.5% (w/w) basic red direct dye, and the composition is pressed into a semi-solid, water disintegratable table.

An example of a preferred embodiment of a condition modifying water dispersible composition for use with a flowing source of water of the present invention comprises about 3% (w/w) Emulgade® 1000NI, about 29% (w/w) PEG-4000, about 7% (w/w) cetiol-C5, about 5% (w/w) Tween-80, about 4.5% (w/w) cetrimonium chloride, about 5% (w/w) nonylphenyl ethoxylate, about 5% (w/w) hydrogenated castor oil, about 1.3% (w/w) phenoxyethanol, about 6% (w/w) alcohol alkoxylate, and about 20% (w/w) plant oil, wherein the composition comprises about 8% (w/w) argan oil.

An example of a preferred embodiment of a condition modifying water dispersible composition for use with a flowing source of water of the present invention comprises about 4% (w/w) Emulgade® 1000NI, about 42% (w/w) PEG-4000, about 5% (w/w) cetiol-C5, about 7% (w/w) cetrimonium chloride, about 3% (w/w) ceteareth-50, about 2% (w/w) hydrogenated castor oil, and about 22% (w/w) plant oil, wherein the composition comprises about 2% (w/w) argan oil.

An example of a preferred embodiment of a condition modifying water dispersible composition for use with a flowing source of water of the present invention comprises about 5.5% (w/w) Emulgade® 1000NI, about 34% (w/w) PEG-4000, about 8% (w/w) cetiol-C5, about 5.5% (w/w) cetrimonium chloride, about 1% (w/w) TERIC® N9,about 10% (w/w) hydrogenated castor oil, about 2.5% (w/w) phenoxyethanol, about 5% (w/w) TERIC® N5, about 5% (w/w) ethylhexyl methoxycinnamate and about 15% (w/w) plant oil.

An example of a preferred embodiment of a condition modifying water dispersible composition for use with a flowing source of water comprises about 4% (w/w) Emulgade® 1000NI, about 40% (w/w) PEG-4000, about 4% (w/w) cetiol-C5, about 6% (w/w) cetrimonium chloride, about 7% (w/w) nonylphenyl ethoxylate, about 11% (w/w) hydrogenated castor oil, about 2.5% (w/w) phenoxyethanol, and about 16% (w/w) plant oil.

An example of a preferred embodiment of a condition modifying water dispersible composition for use with a flowing source of water comprises about 4% (w/w) Emulgade® 1000NI, about 42% (w/w) PEG-4000, about 7% (w/w) cetrimonium chloride, about 2% (w/w) hydrogenated castor oil, and about 25% (w/w) plant oil.

Methods for Making Compositions for Modifying the Hair

Colour modifying compositions of the invention were prepared by first mixing one or more directs dyes with cetrimonium chloride for about 20 minutes at about 80° C. To this mixture is added Emulgade 1000 NI, optionally shea butter and coconut oil, PEG-4000S, Eumulgin B3 and PEG-40 before mixing again for about 20 minutes at about 80° C. To this mixture is then added one or more plant oils, before mixing again for about 5 minutes at about 80° C. and cooling the mixture to 60° C. To this mixture is then added one or more emollients and/or keratin, before mixing again for about 15 minutes at about 60° C. and cooling the mixture to 52° C., prior to the composition being pressed into a semi-solid, water disintegratable table.

Method of Hair Colouration

In a preferred embodiment of the present invention, there is also provided a method of hair colouration comprising the steps of adding the above-described water dispersible composition to a shower head and applying the dose of water dispersed colour or condition modifier to the hair as a continuous dose of flowing water dispersed colour or condition modifier.

Although the invention has been described with reference to specific examples it will be appreciated by those skilled in the art that the invention may be embodied in many other forms.

We claim:
1. A method of modifying the colour of hair, comprising:
applying to the hair a flowing dose of water dispersed hair colour modifier from a water dispersible composition, the composition comprising:
a colour modifier, a thickening agent, a rheology modifier and an emulsifier,
wherein the composition is provided in the form of a water-disintegrable tablet, and
wherein the colour modifier comprises 0.1%-95% (w/w) of pigment, temporary dye, semi-permanent dye, demi-permanent dye, permanent dye or a combination of any two or more thereof.
2. The method of claim 1, wherein the composition is contained in a porous bag.
3. The method of claim 1, wherein the composition is contained in a pervious vesicle that allows water to flow through it, wherein the pervious vehicle is a showerhead.
4. The method of claim 1, wherein the colour modifier comprises one or more compounds selected from the group consisting of a lifting agent, a bleaching agent, and a stripping agent.
5. The method of claim 1, wherein the composition comprises a lipid-rich thickening agent at a concentration of about 1%-15% (w/w), one or more plant oils at a concentration of about 20%-35% (w/w), a water soluble, organic rheology modifier at a concentration of about 30%-45% (w/w), and a colour modifier at a concentration of about 0.5% - 15% (w/w), wherein the colour modifier comprises two or more compounds selected from the group consisting a lifting agent, a bleaching agent, a stripping agent, a dye and a pigment.
6. The method of claim 1, wherein the composition comprises one or more emulsifiers at a total concentration of about 10%-20% (w/w), a lipid-rich thickening agent at a concentration of about 1%-5% (w/w), a water soluble, organic rheology modifier at a concentration of about 40%-45% (w/w), and a colour modifier at a concentration of about 1%-20% (w/w).
7. The method of claim 1, wherein the composition comprises one or more cationic and/or non-ionic emulsifiers at a concentration of about 10%-20% (w/w), hydrogenated castor oil at a concentration of about 1%-5% (w/w), one or more plant oils at a concentration of about 15%-35% (w/w), a polyethylene glycol at a concentration of about 30% - 45% (w/w), and a colour modifier at a concentration of about 0.5%-10% (w/w).
8. The method of claim 1, wherein the composition comprises 15-20% (w/w) emulsifier, 40-45% (w/w) rheology modifier, 2.5% (w/w) thickening agent, 25-35% (w/w) plant oil, and 0.1-3% (w/w/) colour modifier, wherein the colour modifier is a semi-permanent or demi-permanent dye, or a combination thereof, and the composition is pressed into a semi-solid, water disintegratable tablet.
9. The method of claim 1, wherein the composition comprises 4.5% (w/w) ceteareth-20/cetearyl, about 44% (w/w) PEG-4000, about 4% (w/w) coconut oil or cetiol-C5, about 2.5% (w/w) hydrogenated castor oil, about 3% (w/w)

ceteareth-30, and about 25%-30% (w/w) plant oil, and 0.1-3% (w/w/) direct dye, wherein the direct dye is a semi-permanent dye, demi-permanent dye, or temporary dye, a combination thereof, and the composition is pressed into a semi-solid, water disintegratable tablet.

10. A water dispersible composition comprising a hair colour modifier, a thickening agent, an emulsifier and a rheology modifier, when used in the method of claim 1.

* * * * *